US008939940B2

(12) United States Patent
Haury et al.

(10) Patent No.: US 8,939,940 B2
(45) Date of Patent: Jan. 27, 2015

(54) BLOW-MOLDED SYRINGE FOR USE WITH INJECTORS

(75) Inventors: John A. Haury, Sewickley, PA (US); Edward J. Rhinehart, Monroeville, PA (US); Samuel L. Belcher, Moscow, OH (US)

(73) Assignee: Bayer Medical Care Inc., Indianola, PA (US)

(*) Notice: Subject to any disclaimer, the term of this patent is extended or adjusted under 35 U.S.C. 154(b) by 427 days.

(21) Appl. No.: 12/794,990

(22) Filed: Jun. 7, 2010

(65) Prior Publication Data

US 2010/0241085 A1 Sep. 23, 2010

Related U.S. Application Data

(62) Division of application No. 11/833,427, filed on Aug. 3, 2007, now Pat. No. 7,740,792.

(60) Provisional application No. 60/821,314, filed on Aug. 3, 2006.

(51) Int. Cl.
*A61M 5/00* (2006.01)
*B29C 49/00* (2006.01)
(Continued)

(52) U.S. Cl.
CPC ............ *B29C 49/0073* (2013.01); *A61M 5/007* (2013.01); *A61M 5/14546* (2013.01); *A61M 5/14566* (2013.01); *B29B 11/08* (2013.01); *B29B 11/10* (2013.01); *B29B 11/14* (2013.01); *B29B 2911/14053* (2013.01); *B29B 2911/14066* (2013.01); *B29B 2911/1408* (2013.01); *B29B 2911/14093* (2013.01); *B29B 2911/14113* (2013.01); *B29B 2911/1412* (2013.01); *B29B 2911/1414* (2013.01); *B29B 2911/14146* (2013.01); *B29B 2911/14166* (2013.01);
(Continued)

(58) Field of Classification Search
CPC ............ A61M 5/007; A61M 5/14546; A61M 5/14566; B29B 11/08; B29B 11/10; B29B 11/14; B29B 2911/14053; B29B 2911/14066; B29B 2911/1408; B29B 2911/14093; B29B 2911/14113; B29B 2911/1412; B29B 2911/1414
USPC .................. 604/187, 216, 218, 72, 146, 181; 264/532, 537, 524, 535
See application file for complete search history.

(56) References Cited

U.S. PATENT DOCUMENTS 3,256,892 A 11/1962 Esposito, Jr.
3,376,999 A * 4/1968 De Hart et al. ............... 222/135
(Continued)

*Primary Examiner* — Theodore Stigell
*Assistant Examiner* — Imani Hayman
(74) *Attorney, Agent, or Firm* — David Schramm; Joseph L. Kent; James R. Stevenson

(57) ABSTRACT

A syringe for use in the pressurized injection of a fluid. The syringe includes a syringe barrel composed of a polymeric material having undergone expansion via blow molding, and an injection molded attachment mechanism which is integral with the syringe barrel and is located at the proximal end of the syringe barrel. The syringe barrel has a consistent wall thickness and is capable of withstanding pressures of at least 1200 psi. The syringe barrel includes a biaxial stretch sidewall as a result of the blow molding process while the attachment mechanism remains essentially unchanged by the blow molding process. The polymeric material can be, for example, polyethyleneterephthalate, cyclic olefin polymer, polypropylene, polystyrene, polyvinylidene chloride, polyethylene naphthalate and/or nylon.

20 Claims, 7 Drawing Sheets

(51) Int. Cl.

| | |
|---|---|
| *B29C 45/00* | (2006.01) |
| *A61M 5/145* | (2006.01) |
| *B29B 11/08* | (2006.01) |
| *B29B 11/10* | (2006.01) |
| *B29B 11/14* | (2006.01) |
| *B29C 49/04* | (2006.01) |
| *B29C 49/06* | (2006.01) |
| *B29C 49/12* | (2006.01) |
| *B29C 49/22* | (2006.01) |
| *B29K 23/00* | (2006.01) |
| *B29K 25/00* | (2006.01) |
| *B29K 27/00* | (2006.01) |
| *B29K 67/00* | (2006.01) |
| *B29K 77/00* | (2006.01) |
| *B29L 31/00* | (2006.01) |

(52) U.S. Cl.
CPC ............... *B29B2911/14173* (2013.01); *B29B 2911/14326* (2013.01); *B29B 2911/14333* (2013.01); *B29B 2911/14366* (2013.01); *B29B 2911/144* (2013.01); *B29B 2911/1442* (2013.01); *B29B 2911/1446* (2013.01); *B29B 2911/14486* (2013.01); *B29C 49/04* (2013.01); *B29C 49/06* (2013.01); *B29C 49/12* (2013.01); *B29C 49/22* (2013.01); *B29C 49/221* (2013.01); *B29K 2023/086* (2013.01); *B29K 2023/12* (2013.01); *B29K 2025/00* (2013.01); *B29K 2027/08* (2013.01); *B29K 2067/00* (2013.01); *B29K 2077/00* (2013.01); *B29L 2031/7544* (2013.01)
USPC ............ 604/187; 264/532; 264/535; 264/537

(56) References Cited

U.S. PATENT DOCUMENTS

| | | | |
|---|---|---|---|
| 3,855,380 A | 12/1974 | Gordon et al. | |
| 3,923,943 A | 12/1975 | Iriko et al. | |
| 4,039,641 A | 8/1977 | Collins | |
| 4,244,409 A | 1/1981 | Wilson et al. | |
| 4,342,184 A | 8/1982 | Van Eck et al. | |
| 4,411,656 A | 10/1983 | Cornett, III | |
| 4,681,606 A | 7/1987 | Swan, Jr. et al. | |
| 5,047,017 A * | 9/1991 | Koska ..................... | 604/110 |
| 5,122,327 A | 6/1992 | Spina et al. | |
| 5,242,422 A | 9/1993 | Schneberger et al. | |
| 5,330,425 A | 7/1994 | Utterberg | |
| 5,383,858 A | 1/1995 | Reilly et al. | |
| 5,873,861 A | 2/1999 | Hitchins et al. | |
| 5,900,205 A | 5/1999 | Sadr et al. | |
| 6,017,330 A | 1/2000 | Hitchins et al. | |
| 6,041,775 A * | 3/2000 | Century ................. | 128/200.14 |
| 6,224,577 B1 | 5/2001 | Dedola et al. | |
| 6,394,983 B1 | 5/2002 | Mayoral | |
| 6,652,489 B2 | 11/2003 | Cowan et al. | |
| 6,665,489 B2 | 12/2003 | Collart | |
| 6,673,303 B2 | 1/2004 | White et al. | |
| 6,719,733 B1 | 4/2004 | Heffernan et al. | |
| 6,984,222 B1 | 1/2006 | Hitchins et al. | |
| 7,175,609 B1 | 2/2007 | Gray | |
| 7,740,792 B2 | 6/2010 | Haury et al. | |
| 2002/0048642 A1 | 4/2002 | Beck | |
| 2002/0055719 A1 | 5/2002 | Lo | |
| 2004/0262818 A1 | 12/2004 | Takeuchi | |
| 2005/0148720 A1* | 7/2005 | Li et al. ................. | 524/474 |
| 2005/0161866 A1 | 7/2005 | Batlaw et al. | |
| 2006/0029720 A1* | 2/2006 | Panos et al. ............ | 427/2.1 |
| 2008/0157444 A1 | 7/2008 | Melsheimer | |
| 2008/0200916 A1* | 8/2008 | Murphy ................... | 606/94 |

* cited by examiner

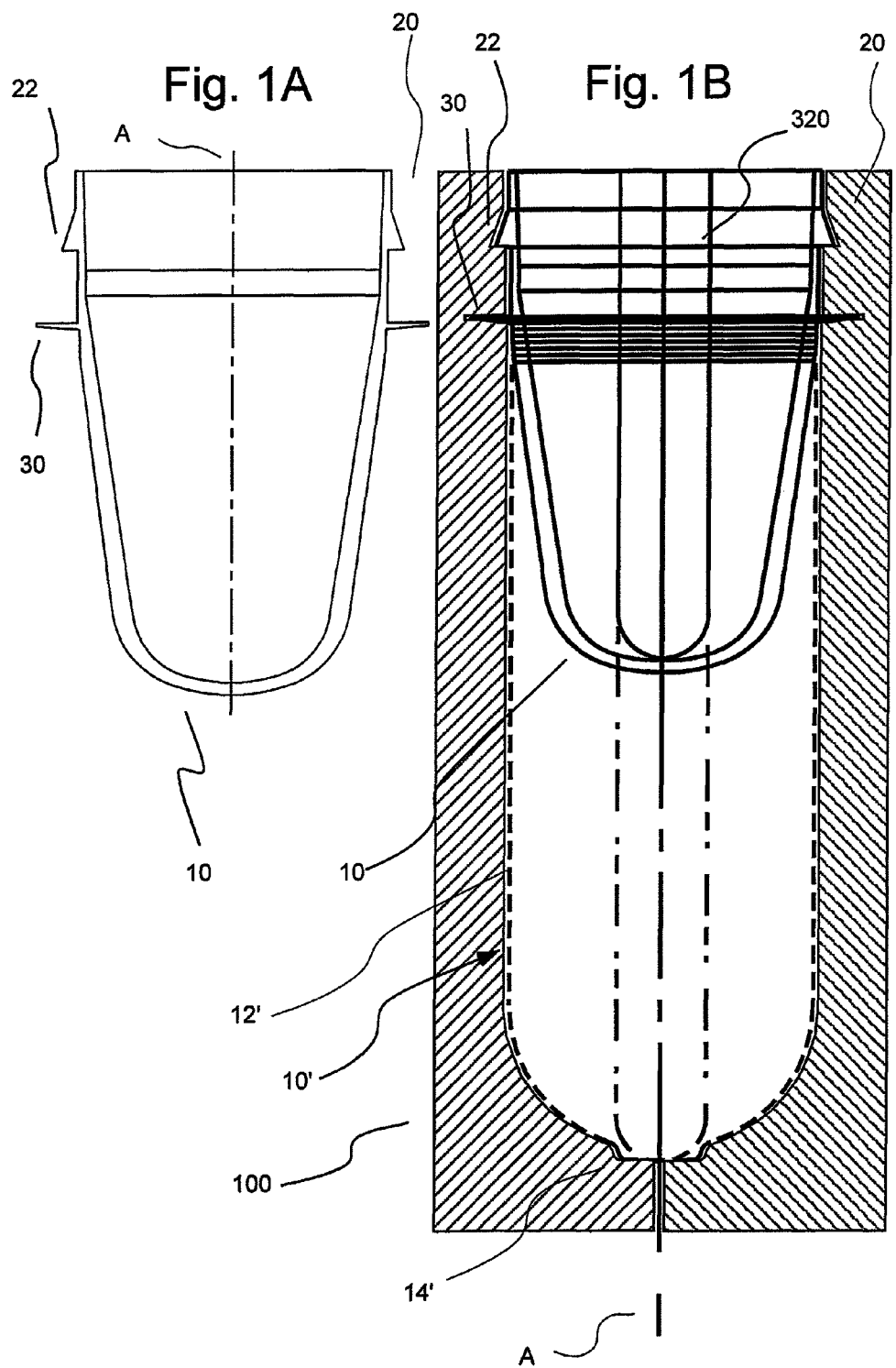

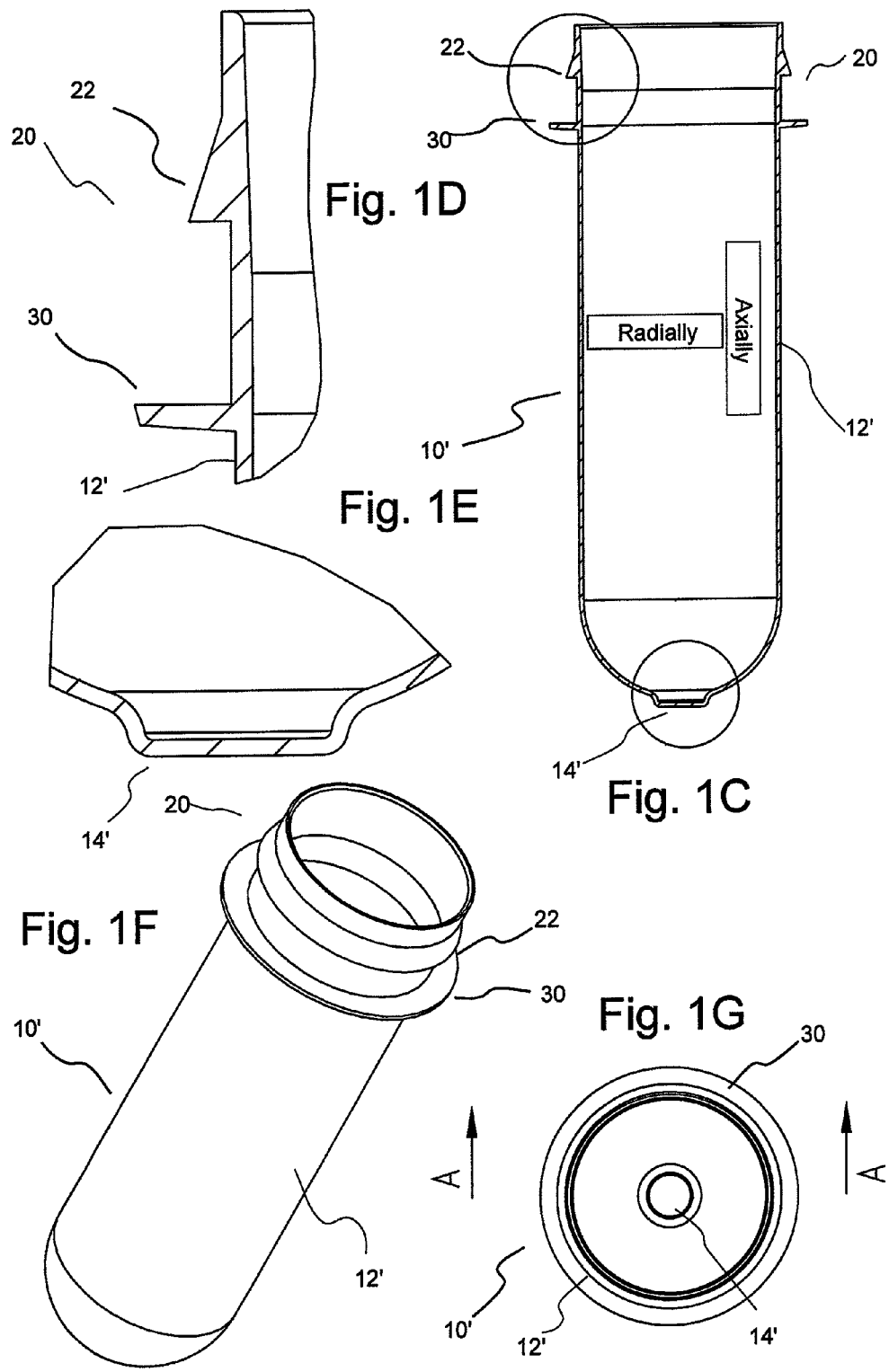

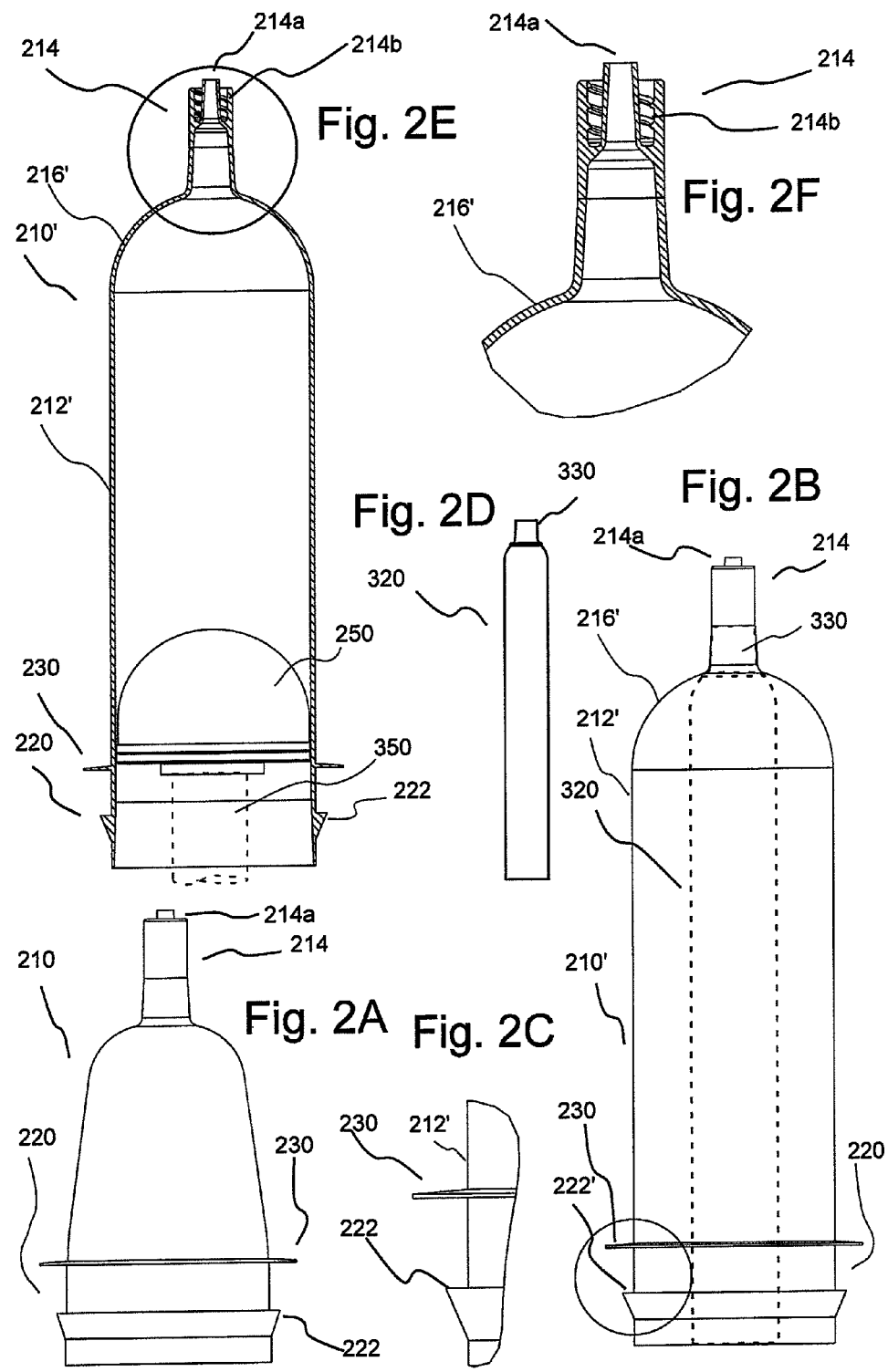

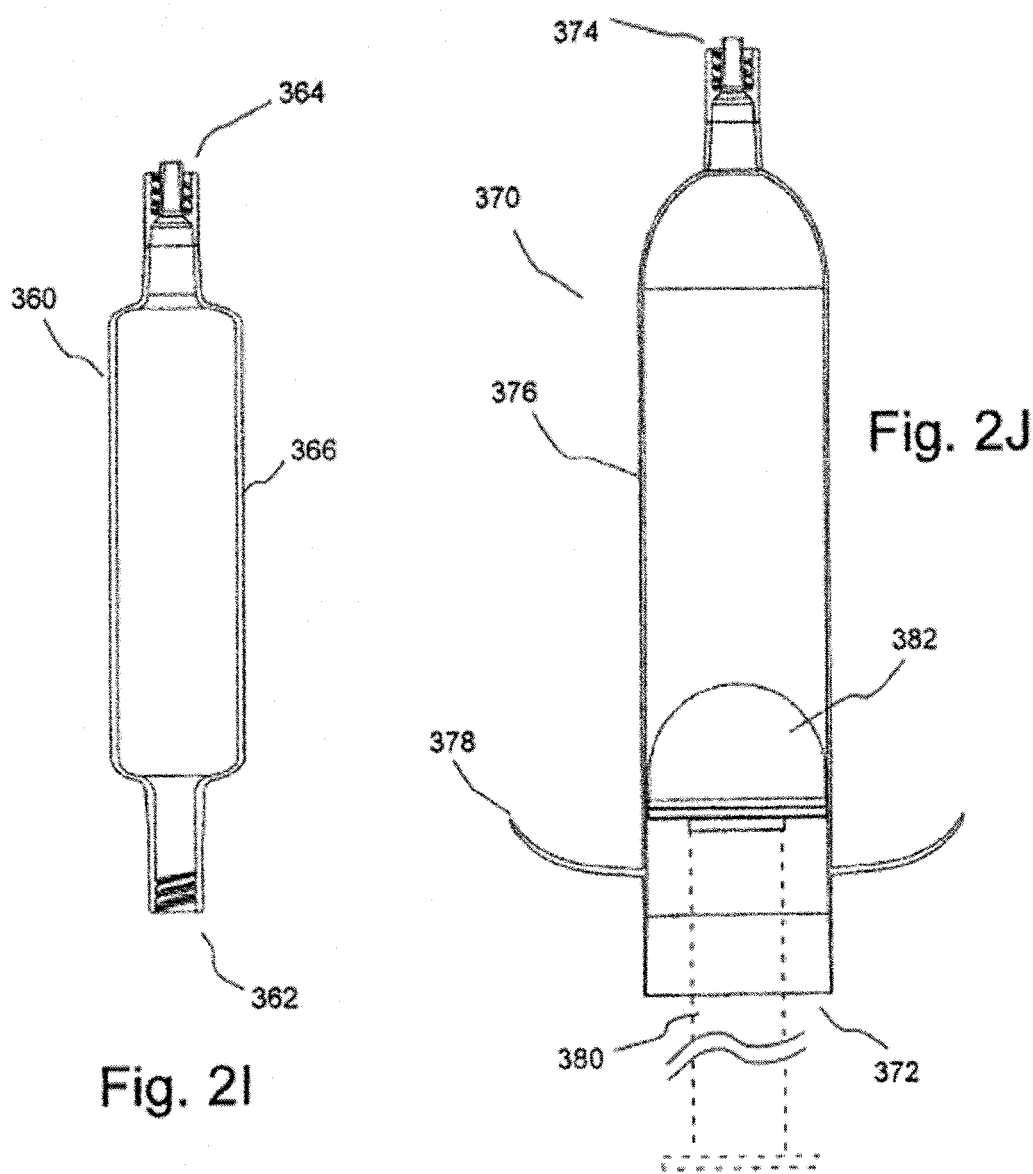
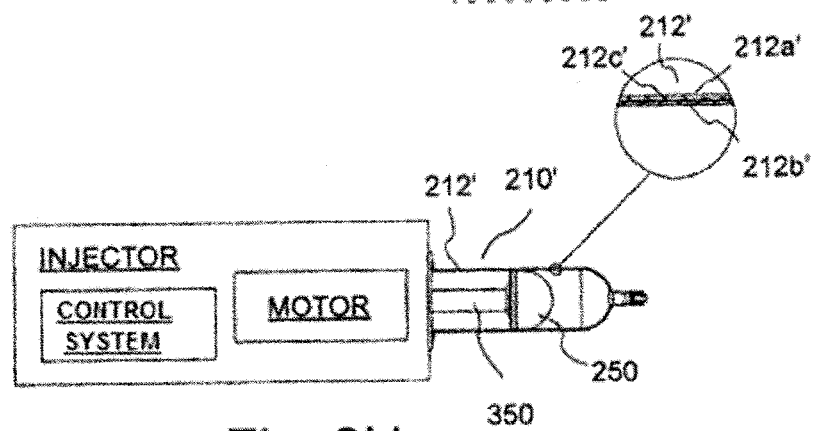

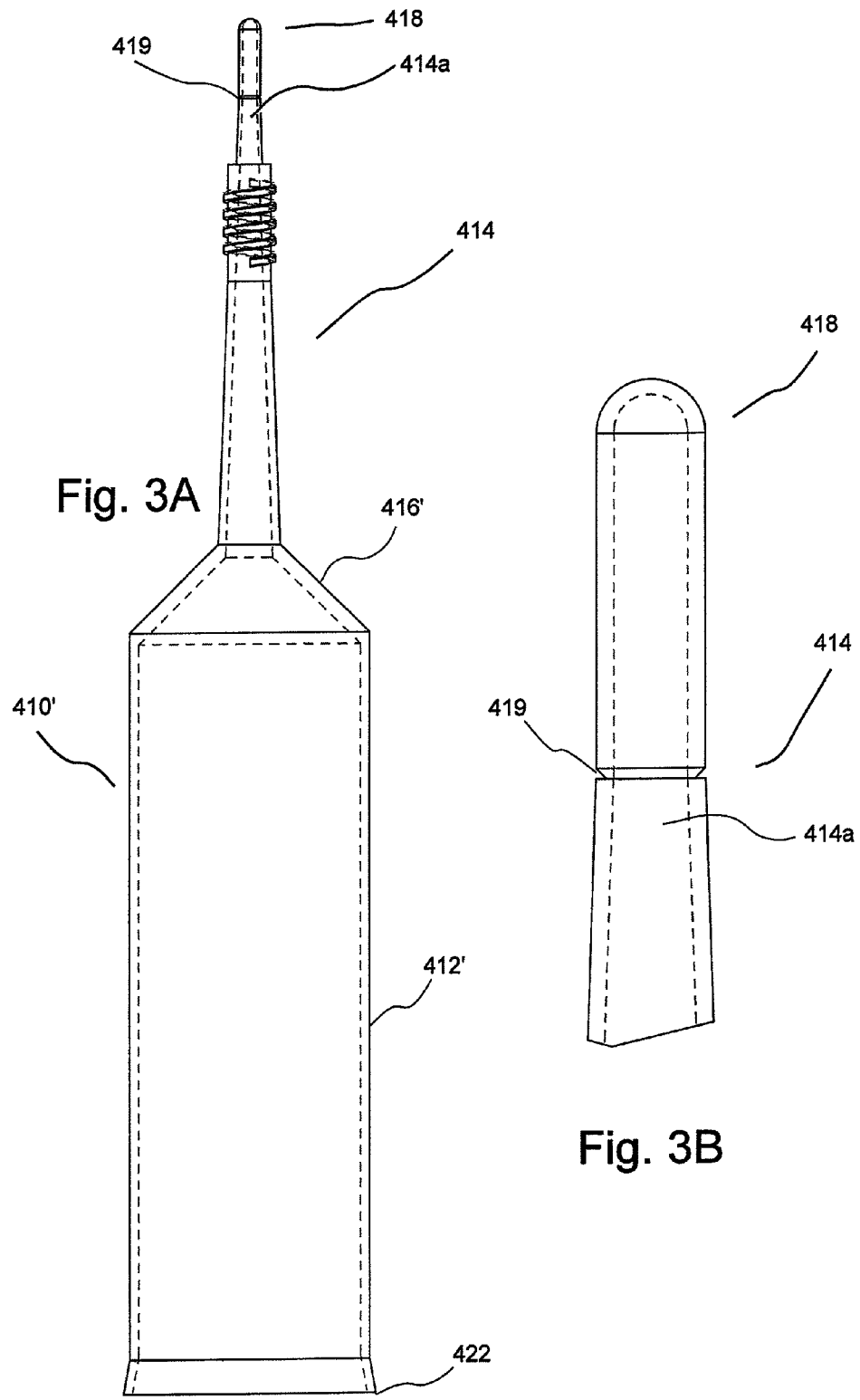

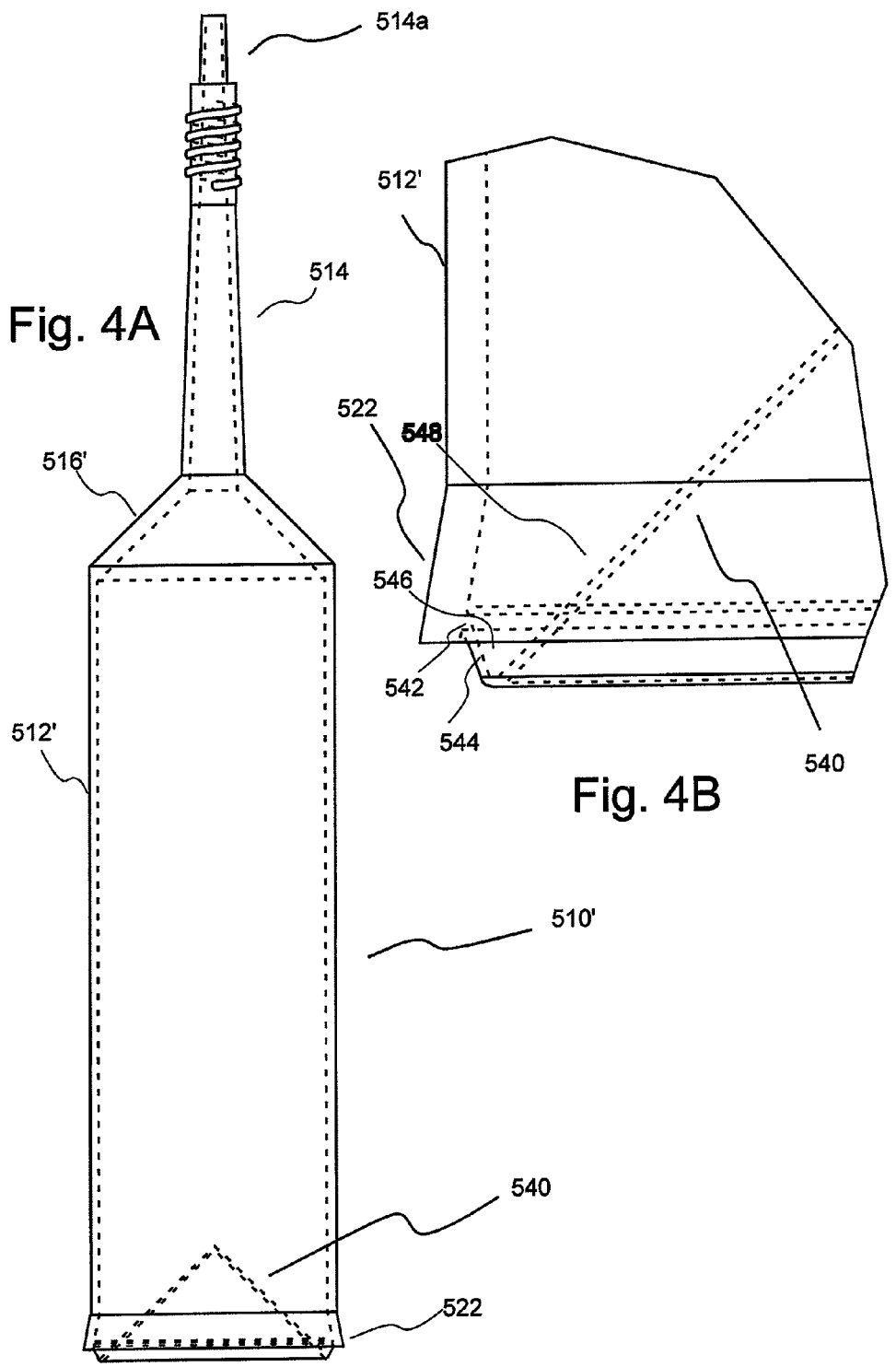

BLOW-MOLDED SYRINGE FOR USE WITH INJECTORS

CROSS REFERENCE TO RELATED APPLICATION(S)

This application is a divisional of U.S. patent application Ser. No. 11/833,427, filed Aug. 3, 2007, now patented, and claims the benefit of U.S. Provisional Patent Application Ser. No. 60/821,314, filed Aug. 3, 2006, the disclosures of which are incorporated herein by reference.

BACKGROUND OF THE INVENTION

The present invention relates generally to syringes for use with injectors and to methods of manufacturing syringes and other devices and, particularly, to syringes manufactured by blow molding and to methods of blow molding syringes and other devices.

In many medical procedures, such as drug delivery, it is desirable to inject a fluid into a patient. Likewise, numerous types of contrast media (often referred to simply as contrast) are injected into a patient for many diagnostic and therapeutic procedures for example, gene therapy, cell and biological agent delivery, and delivery of a therapeutic agents generally). For example, contrast media are used in diagnostic procedures such as X-ray procedures (including, for example, angiography, venography, urography), computed tomography (CT) scanning, magnetic resonance imaging (MRI), and ultrasonic imaging. Contrast media are also used during therapeutic procedures, including, for example, angioplasty and other interventional radiological procedures.

A number of injector-actuated syringes and powered injectors for use in medical procedures such as angiography, computed tomography (CT), ultrasound and NMR/MRI have been developed. A front-loading syringe and injector system is, for example, disclosed in U.S. Pat. No. 5,383,858, assigned to the assignee of the present invention, the disclosure of which is incorporated herein by reference. Other front-loading syringes and injectors systems are, for example, disclosed in U.S. Pat. No. 6,652,489, the disclosures of which are incorporated herein by reference.

Historically, it has been difficult to manufacture syringes with desirable transparent optical properties that exhibit sufficient strength for use with front-loading, pressure jacketless injectors. Indeed, depending upon the application, syringe pressures in the range of 300 psi to 1200 psi are commonly experienced in injection procedures using powered injectors. Typically, to achieve suitable strength, the syringe walls must be thickened during manufacture, which increases costs and, depending upon the material, can degrade optical properties. However, in the current injection molding practices for manufacturing syringe, there is a limit to the wall thickness that can be achieved. This limit can result in syringes designed with a lower safety factor than desirable. Moreover, as wall thickness is increased, production costs also increase. For example, increases in wall thickness are associated with longer injection times, longer packing times, higher pressures, longer cooling time and increased resin costs.

It is desirable to develop new syringes and methods of fabricating or manufacturing syringes that reduce or eliminate the above-identified and other problems associated with current syringes and methods of manufacture.

SUMMARY OF THE INVENTION

In one aspect, the present invention provides a syringe for use in a pressurized injection of a fluid. The syringe includes a syringe barrel including a polymeric material having undergone expansion via blow molding. An inner diameter of the syringe barrel can, for example, be sufficiently constant (over at least a portion of the axial length of the syringe) that a plunger slidably positioned within the syringe barrel and in generally sealing contact with an inner wall of the syringe barrel can be used within the syringe barrel to generate a pressure to inject a fluid contained within the syringe barrel. The syringes of the present invention can be used in both low pressure and high pressure application. For example, the constancy of the inner diameter of the syringe barrels of the syringes of the present invention is suitable to generate a pressure of at least 1 psi within the syringe barrel or of, for example, at least 100 psi within the syringe barrel. In several embodiments, the diameters of the inner walls of the syringe barrels of the present invention are suitably constant to generate a pressure of at least 200 psi, at least 300 psi, or even at least 500 psi within the syringe barrel.

The inner diameter of the syringe wall can, for example, vary no more than 0.01 in. The inner diameter of the syringe can also vary by no more than 0.007 in. or even no more than 0.004 in.

The polymeric material can, for example, undergo biaxial orientation via injection stretch blow molding.

The syringe can, for example, include one or more portions, sections or components that are molded to certain predefined acceptable tolerances for a predefined use. Such molded portions, sections or components are sometimes referred to herein as "precision molded" portions, sections or components. For example, the syringe can include one or more attachment mechanisms positioned, for example, to the rear of the syringe barrel. Likewise, one or more attachment mechanism and/or other precision molded portions can be formed on or in the vicinity of the forward end of the syringe, in the vicinity of the syringe outlet.

In several embodiments, the polymeric material of the syringe includes, for example, at least one of polyethyleneterephthalate (PET), cyclic olefin polymer, polypropylene, polystyrene, polyvinylidene chloride, polyethylene naphthalate (PEN) or nylon. The polymeric material can be a coinjected material of one or more of the above identified polymers and/or other polymers. Examples of coinjected materials include, but are not limited to, PET/PEN or PET/nylon. The syringe can include a first layer of a first polymeric material and at least a second layer of a second polymeric material, different from the first polymeric material. At least one of the first polymeric materials can, for example, include polyethyleneterephthalate, cyclic olefin polymer, polypropylene, polystyrene, polyvinylidene chloride, polyethylene naphthalate or nylon. The first and/or the second polymeric material can, for example, include a single polymer or blends of two or more polymers. As used herein, the term "polymer" includes homopolymers which are synthesized from a single monomer and copolymers which are synthesized from two or more different monomers. The polymeric materials of the first layer and the second layer can, for example, differ in one or more respects such as composition, molecular weight, crystallinity, barrier properties etc.

The syringe barrels can, for example, withstand relatively high pressures. For example, the syringe barrel can withstand pressures of at least 1 psi, at least 100 psi, at least 150 psi, at least 200 psi, at least 300 psi, at least 500 psi or even at least 1200 psi.

The walls of the syringe barrel can be relatively thin. For example, the wall of the syringe barrel can be less than 0.07 inches in thickness or even less than 0.05 inches in thickness.

The method can further include a heat setting process. For example, a heat setting process can be used to maintain a suitable dimension of internal diameter of a syringe barrel (or, for example, other open ended medical devices and other devices). A heat setting process can also, for example, be used to minimize fluid capacitance of a syringe barrel or other open ended medical device (or, for example, other open ended medical devices and other devices).

In another aspect, the present invention provides a method of forming a syringe including the steps of: injection molding at least one polymeric material to form a preform; placing the preform into a blow mold die; and expanding at least a portion of the preform within the die to form a barrel of the syringe. Those components, elements, portions or sections of the preform to be blow molded/expanded (for example, the barrel portion of the syringe) are typically heated (above the glass transition ($T_g$) of the polymeric material(s)) prior to placing the preform within the blow mold die. During the preheating process, precision molded components, portions or sections of the preform can be protected from heating (that is, maintained at a lower temperature) to, for example, maintain molded dimensions within acceptable tolerances. Those portions or sections of the preform to be expanded within the blow mold die can also be heated during the blow molding process. The syringes can be formed for use at low pressure or to withstand relatively high pressures as described above. The at least one polymeric material can, for example, be polyethyleneterephthalate, cyclic olefin polymer, polypropylene, polystyrene, polyvinylidene chloride, polyethylene naphthalate or nylon. The method can further include a heat setting process.

Injection molding the preform can, for example, include forming one or more portions molded to dimension of predefined acceptable tolerance such as an attachment mechanism (positioned, for example, adjacent a proximal or rearward end of the syringe), which is adapted to connect the syringe to, for example, a powered injector. The attachment mechanism can, for example, include at least one flange. The tolerances of precision molded portions such as injector attachment mechanisms are maintained during blow molding. For example, the attachment mechanism or other precision molded portion is not altered or substantially altered (for example, such that an attachment mechanism does not suitably retain the syringe upon an injector) during the expansion of the preform. Injection molding the preform can also include forming a connector or other precision molded portion adjacent a distal end of the preform. The connector or other precision molded portion is not altered or substantially altered during expansion of the preform.

Expanding at least a portion of the preform can include forcing of a gas within the preform and axial extension of an extension rod within the preform. Injection molding the preform can also include forming a syringe outlet section at a distal end of the preform, wherein the preform including a passage between a barrel section thereof and the syringe outlet section. The extension rod can, for example, form at least a partial seal with the passage during expansion of the preform. In several embodiments, injection molding the preform can also include forming a connector or attachment mechanism (for example, a Luer connector) during injection molding of the preform as described above, which is positioned adjacent the distal end of the preform. Once again, the connector is not altered or substantially altered during expansion of the preform.

A removable closure can be formed on a distal end of the outlet section during injection molding. The closure can, for example, be removably connected to the outlet section via a wall section of reduced thickness.

In another aspect, the present invention provides a method of forming a syringe for use with an injector including injection molding a polymeric material to form a removable closure integrally with an outlet section or opening of the syringe. The removable closure can, for example, be formed during injection molding of a preform for the syringe which is subsequently blow molded to form the syringe. As described above, the closure can be removably connected to the outlet section via a wall section of reduced thickness.

In a further aspect, the present invention provides a syringe including a barrel, an outlet section integrally formed with the barrel at a distal end of the barrel and a removable closure integrally formed with the outlet section at a distal end of the outlet section. The closure can, for example, be removably connected to the outlet section via a wall section of reduced thickness.

In another aspect, method of forming a syringe for use with an injector, including: forming a preform comprising a syringe outlet section on a distal end thereof and a closed section corresponding to a precursor of a barrel section of the syringe on the proximal end thereof by injecting at least one polymeric material into a mold for the preform; placing the preform into an blow mold die; and expanding at least a portion of the preform by passing pressurized gas into the interior of the syringe via an outlet opening in the outlet section to form a barrel of the syringe. As described above, those portions or sections of the preform to be blow molded/expanded (for example, the barrel portion of the syringe) are typically heated (above the glass transition ($T_g$) of the polymeric material(s)) prior to placing the preform within the blow mold die. During the preheating process, precision molded components, portions or sections of the preform can be protected from heating (that is, maintained at a lower temperature) to, for example, maintain molded dimensions within acceptable tolerances. Once again, those portions or sections of the preform to be expanded within the blow mold die can also be heated during the blow molding process. The syringe can be formed to withstand low pressures and/or relatively high pressures (for example, pressures of at least 100 psi or higher) as described above. The formed syringe can be closed on the proximal end thereof via a removable closure formed integrally or monolithically with the syringe. The removable closure can, for example, form a plunger section upon removal from connection with the syringe.

In a further aspect, the present invention provides a syringe including an outlet section on a distal end thereof. The outlet section includes an outlet opening. A barrel section is integrally or monolithically formed with the outlet section. A disengeagable closure is integrally or monolithically formed at a proximal end of the syringe. In several embodiments, the closure forms at least part of a syringe plunger upon disengagement from the barrel section.

In still a further aspect, the present invention provides a syringe including a syringe wall comprising a first layer of a first polymeric maternal and at least a second layer of a second polymeric material, different from the first polymeric material. One of the first layer and the second layer can, for example, include polyethyleneterephthalate, cyclic olefin polymer, polypropylene, polystyrene, polyvinylidene chloride, polyethylene naphthalate and/or nylon. The first layer can, for example, be radially inward from the second layer and have greater lubricity than the second layer. One of the first layer and the second layer can, for example, have better barrier properties than the other of the first layer and the second layer.

In still a further aspect, the present invention provides a method of forming a device including a first opening, a second opening and a flow path between the first opening and the second opening. The method includes: injection molding at least one polymeric material to form a preform, the preform including a first molded portion in the vicinity of the first opening that is molded to acceptable tolerances; placing the preform into an blow mold die; and expanding an intermediate portion of the preform intermediate between the first opening and the second opening within the die by blowing a gas into the preform and axially extending an extension rod within the preform. The extension rod abuts a section of the preform and forms at least a partially sealing closure between the flow path and the first opening during extension thereof. The intermediate portion of the preform is expanded while maintaining the acceptable tolerances of the first molded portion. The method can further include heating the intermediate portion of the preform before placing the preform into the blow mold die. The method can also include heating the intermediate portion of the preform during expansion within the die. The method can further include a heat setting process.

In several embodiments, the device is a medical device adapted to form a component of a fluid flow system. In a number of embodiments, the device is a syringe.

The preform can, for example, further include a second molded portion in the vicinity of the second opening that is molded to acceptable tolerances. The intermediate portion of the preform is expanded while maintaining the acceptable tolerances of the second molded portion.

The polymeric material can, for example, include polyethyleneterephthalate, cyclic olefin polymer, polypropylene, polystyrene, polyvinylidene chloride, polyethylene naphthalate and/or nylon.

In still another aspect, the present invention provides a system for forming a device including a first opening, a second opening and a flow path between the first opening and the second opening. The system includes a blow mold die adapted to receive an injection molded preform. The preform further includes a first molded portion in the vicinity of the first opening that is molded to acceptable tolerances. The blow mold die includes a forward section shaped to receive the first molded portion. The system further includes an extension rod axially movable within the blow mold die to assist in axially expanding an intermediate portion of the preform intermediate between the first opening and the second opening within the die while gas is blown into the preform. The extension rod is adapted to abut a section of the preform and form at least a partially sealing closure between the flow path and the first opening during extension thereof. In several embodiments, the blow mold die further includes a rearward section shaped to receive a second molded portion in the vicinity of the second opening that is molded to acceptable tolerances. Cooperation between the rearward section and the second molded portion can, for example, operate to retain the preform in the blow mold die during expansion of the intermediate section. The method can further include a heat setting process.

BRIEF DESCRIPTION OF THE DRAWINGS

Other aspects of the invention and their advantages will be discerned from the following detailed description when read in connection with the accompanying drawings, in which:

FIG. 1A illustrates an embodiment of a preform of the present invention.

FIG. 1B illustrates the stretch blow molding of the preform of FIG. 1A into a mold to form a syringe.

FIG. 1C illustrates a side, cross-sectional view of the syringe of FIG. 1B.

FIG. 1D illustrates a cross-sectional enlargement of the rearward end of the syringe of FIG. 1C.

FIG. 1E illustrates a cross-sectional enlargement of the forward end of the syringe of FIG. 1C.

FIG. 1F illustrates a perspective view of the syringe of FIG. 1C.

FIG. 1G illustrates a front view of the syringe of FIG. 1C.

FIG. 2A illustrates another embodiment of a preform of the present invention.

FIG. 2B illustrates the stretch blow molding syringe formed from the preform of FIG. 2A with the stretch rod therein.

FIG. 2C illustrates an enlargement of the rearward end of the syringe of FIG. 2B.

FIG. 2D illustrates a side view of the stretch rod.

FIG. 2E illustrates a side cross-sectional view of the syringe of FIG. 2B.

FIG. 2F illustrates a cross-sectional enlargement of the syringe of FIG. 2B.

FIG. 2H illustrates the syringe of FIG. 2B in operative connection with an injector.

FIG. 2I illustrates a blow molded fluid path element of the present invention including a precision molded Luer connection in the vicinity of one of two openings thereof and a precision molded threading connection in the vicinity of the other of the two openings.

FIG. 2J illustrates a blow molded manually operated syringe of the present invention.

FIG. 3A illustrates another embodiment of a syringe of the present invention including an integral syringe tip closure.

FIG. 3B illustrates an enlarged view of the syringe tip of the syringe of FIG. 3A.

FIG. 4A illustrates another embodiment of a syringe of the present invention including an integral rearward closure.

FIG. 4B illustrates an enlarged view of the rearward section of the syringe of FIG. 4A.

DETAILED DESCRIPTION OF THE INVENTION

Figure 2G:
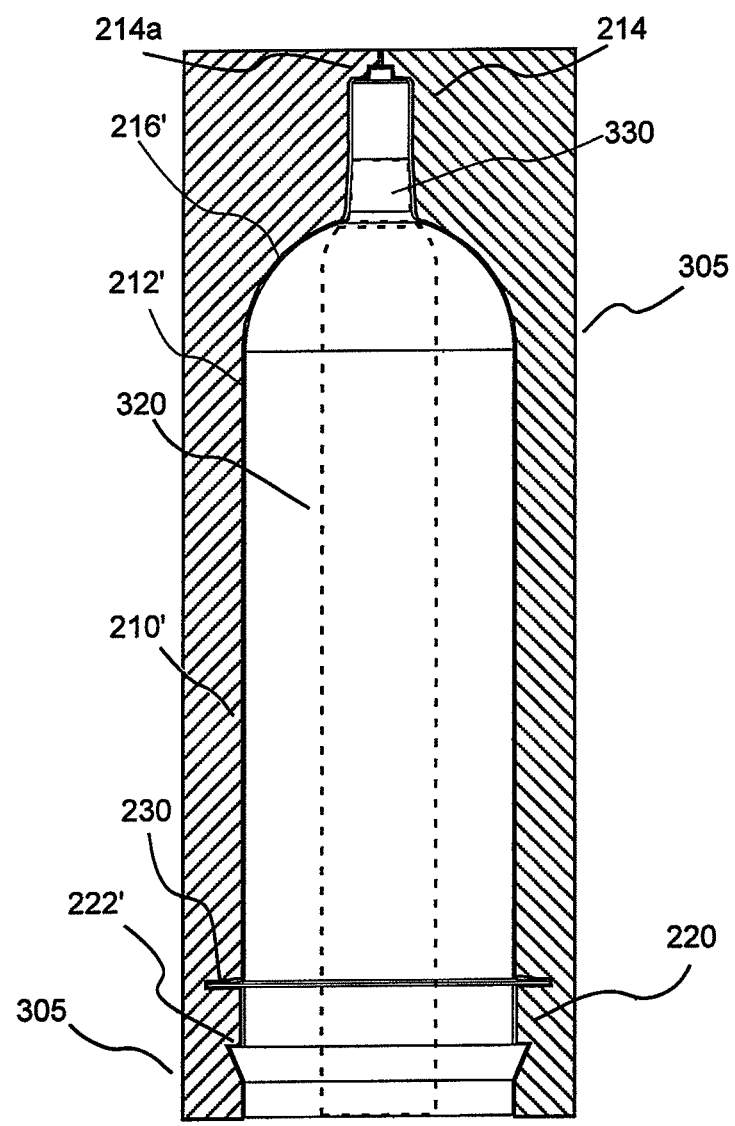
FIG. 2G illustrates the stretch blow molding syringe of FIG. 2A within the mold therefor.

In general, the present invention provides hollow article devices such as syringes and methods of manufacture of such devices using blow molding processes. The present invention is discussed below primarily with reference to representative embodiments of syringes for injection of a fluid into a patient. However, one skilled in the art appreciates that the methods of the present invention can be used to form a number of hollow article devices (including, for example, medical flow path elements or devices).

Blow molding is a method of forming hollow articles from polymeric (thermoplastic) materials. Simplifying, the blow molding process involves forming a heated tube within a mold cavity using a pressurized gas (typically, compressed air). The three most common methods of blow molding are extrusion blow molding, injection blow molding and injection-stretch blow molding. In extrusion blow molding, tubes or parisons are extruded into alternating open mold halves and then blown and cooled prior to removal from the mold. In injection blow molding, a "preform" component is first injection molded. The preform is then blown to the product's final shape. Injection blow molding can provide dimensional precision in certain critical areas. The injection blow molding process can be performed using separate machines or through use of shuttling or rotating molds. In the injection-stretch blow molding process, a preform is, once again, first injection molded. During subsequent blowing, however, the preform/parison is mechanically extended at an optimal temperature, while radially blown to shape within the mold. Injection-stretch blow molding provides a biaxial stretch to enhance material properties. For example, the biaxial orientation can increase tensile strength by an order of five or more. Furthermore, biaxial orientation can enhance other material properties, such as clarity, barrier properties (2× or more), and mechanical properties. For example, crystallinity of certain polymers can be controlled. In several embodiments for syringes of the present invention manufactured from, for example, polyethyleneterephthalate, crystallinity can be increased to as high as approximately 43% (for example, via mechanical and/or thermal processing) to maximize these improvements. One skilled in the art also realizes that further increasing crystallinity can be detrimental and decrease optical properties and cause the material to be too brittle.

The present inventors have discovered that the improved mechanical properties provided by blow molding of, for example, syringes can enable a decrease in the barrel wall thickness of a syringe as compared to an injection molded syringe while maintaining an acceptable safety factor over a range of operating pressures. Moreover, use of a blow molding process in the manufacture of syringes and other devices can substantially increase manufacturing throughput. Indeed, significant reduction in manufacturing cost can result from using a blow molding process to manufacture syringes for use with powered injectors and non-powered or manually powered syringes. Likewise, significant reduction in manufacturing cost can result from using a blow molding process to manufacture other devices including, but not limited to, hollow devices used in flow paths for medical fluids.

FIGS. 1A through 1G illustrate one embodiment of a preform 10 and a blow molded, closed-ended syringe 10' that was used in several studies of the present invention. Preform 10 was first molded using an injection molding process. The injection molding process facilitates the formation of areas wherein dimensions are critical (that is, areas in which certain dimensional tolerances must be maintained), such as the injector or other attachment mechanism 20 on the rearward end of preform 10. In the embodiment of FIGS. 1A through 1G, injector attachment mechanism 20 includes a flange 22 that extends around the circumference of preform 10 and syringe 10'. Preform 10 and syringe 10' also include a drip flange 30 that cooperates with a front wall of an injector (not shown) to, for example, assist in accurately positioning syringe 10' within the injector and to prevent fluids from entering the injector housing. Injector attachment or mounting flange 22 and drip flange 30 remain essentially unchanged from preform 10 to blow molded syringe 10'. Syringes including such an injector attachment design and injectors for use therewith are described, for example, in U.S. Pat. Nos. 5,383,858 and 6,665,489, the disclosures of which are incorporated herein by reference. As further discussed below, one skilled in the art appreciates that syringes having virtually any type of attachment mechanism and/or one or more other precision molded, elements portions or sections can be manufactured using the methods and systems of the present invention.

FIG. 1B illustrates preform 10 within a mold 100 in which it undergoes stretch blow molding to result in syringe 10'. In FIG. 1B, preform 10 is illustrated in thickened lines for clarity. Likewise, barrel 12' of syringe 10' is illustrated in thickened dashed lines for clarity. Barrel 12' included a forward closed end 14' in this embodiment. Mounting flange 22 and drip flange 30 cooperated with corresponding retaining flanges in mold 100 to retain the rearward end of preform 10 and syringe 10' throughout the stretch blow molding process. Once again, mounting flange 22 and drip flange 30 (and/or other molded elements which are molded to have certain dimensions and associated tolerances) remain essentially unchanged during the stretch blow molding process. In that regard, it may be desirable to maintain the preheat temperature in the rearward portion of preform 10 and syringe 10' relatively cool (below the $T_g$ of the material) as compared to the remainder of the mold to prevent deformation of mounting flange 22 and drip flange 30 (and/or other elements) during the blowing process. Heat shielding can also be used. In general, those sections of mold 100 forward of drip flange 30 are preheated in a preheating unit to a temperature sufficiently high to maintain the temperature of the preform/syringe above the glass transition ($T_g$) of the thermoplastic during the molding process. After preheating, preform 10 is placed into mold 100. In several studies of the present invention, there was no further heating in mold 100. In a number of studies of the present invention, polyethyleneterephthalate (PET) or cyclic olefin polymer (COP) was used. The COP used was ZEONOR® 1410R available from Zeon Chemicals LP of Louisville, Ky. COP is, for example, suitable for sterilization (for example, high energy sterilization (such as radiation), chemical sterilization (such as ethylene oxide), autoclave sterilization and/or steam sterilization) and can, for example, be used in connection with prefillable syringes. As clear to one skilled in the art, a variety of polymeric materials can be used in the devices, systems and methods of the present invention. In general, materials that can undergo orientation (for example, biaxial orientation) during the molding process can be preferred in certain uses because of the enhanced properties exhibited by such materials. In addition to PET and COP, such materials include, but are not limited to, polypropylene, polystyrene and polyvinylidene chloride (PVDC).

As described above, during the stretch blow molding process, stretch rod 320 is extended forward, while compressed air is blown into the interior of preform 10 until preform 10 is expanded to fill the mold cavity, thereby forming syringe 10' including barrel 12' in which the thermoplastic is biaxially oriented (that is, oriented axially or in the direction of axis A and radially/tangentially or in a direction normal or around to axis) as described above. In this embodiment, stretch rod 320 pushes against closed end 14' during the blow stretch molding process. Upon cooling, syringe 10' is removed from mold 100.

To achieve high pressures, smooth plunger movement within the syringe, limit blow by, and/or provide predictable volume in the syringes of the present invention, it is desirable to have an inner diameter in the syringe barrel having a relatively consistent wall thickness. To ensure a relatively consistent wall thickness and therefore a predictable, relatively consistent interior syringe barrel diameter with adequate strength, the preform design is important. For example, the area in front of the drip flange 30 may undergo a stretch of up to four (4) times its original length and width in preform 10 to meet the final dimensions in syringe 10'. If the material stretches unevenly as a result of design or heating limitations, such stretching variability must be provided for in the preform design. For example, additional material may be required in areas of high stretch. On the other hand, reduced material may be required in areas of low stretch. Alternatively or additionally, the rate or speed of stretch, the preform temperature, and blow pressure can be varied. The inventors of the present invention have discovered that relatively consistent and predictable wall thickness and internal diameter can be readily achieved in blow molded syringes. The process considerations set forth above are known to those skilled in the blow molding arts and can result in a syringe barrel compatible with high-pressure (for example, 50 psi to 1500 psi) use and adequate/predictable fluid performance. An example of an acceptable delivery volume tolerance in an injection system is approximately ±2%+1 mL. In meeting a suitable delivery volume tolerance, the inner diameters of the syringes of the present invention preferably do not vary by greater than 0.01 inches. Variances of no greater than 0.007 inches in inner diameter are also achievable. Indeed, variances of no greater than 0.004 inches in inner diameter are also achievable over the pressurizing zone of the syringe.

In several studies of the syringes of FIGS. 1A through 1B, 60 blow molded syringes were used and divided into 3 lots of differing PET fabrication material of 20 syringes each. Preferably, the PET material exhibited partial crystallinity after blow molding. The three PET materials used to fabricate the syringes EN001 PET, EN063 PET and HW CF746 PET, available Eastman Chemical of Kingsport, Tenn. The syringes tested had a wall thickness of approximately 0.030 in. In pressure testing the syringe, triple seal RTF plunger as described, for example, in U.S. Pat. Nos. 5,873,861, 6,017,330 and 6,984,222, the disclosures of which are incorporated herein by reference. Many other plungers, including other dynamically sealing plungers as, for example, described in U.S. Pat. No. 6,224,577, the disclosure of which is incorporated herein by reference, can also be used effectively in the syringes of the present invention. A universal tensile testing machine available from Instron of Norwood, Mass. was used in the testing. Samples for tensile strength testing were cut for testing using a die as known in the art. Several properties of the PET materials studied in the present invention are set forth below in Table 1 as determined using the test conditions and procedures of ASTM D 638, the disclosure of which is incorporated herein by reference. In the case that PET polymers or copolymers are used, such polymer can, for example, have an intrinsic viscosity in the range of 0.65 to 1.04 dl/g (deciliters/gram). As known in the art, intrinsic viscosity is dependent upon the length of the polymer chains of the polymer.

TABLE 1

|  | EN001 | EN063 | HW CF746 |
|---|---|---|---|
| Stress @ yield (psi) | 8,400 | 8,400 | not available |
| Stress @ break (psi) | 3,600 | 4,600 | not available |
| Modulus (psi) | 350,000 | 360,000 | not available |

Static high pressure testing was performed at 2 mL/s for 5 samples from each lot using water. In the static high pressure test, each syringe was filled to just below drip flange (approximately 75% full). The plunger was then installed. The syringe was retained in a holding fixture in the Instron universal tensile testing machine while a measurable force was applied to plunger. The Instron universal tensile testing machine, which was calibrated for flow rate, was set at 2 ml/sec and failure mode was recorded. Three PET material types, as described above, were tested. The static high pressure testing resulted in an average pressure of 342 psi with a standard deviation of 40 psi for EN001 PET. Failure modes were barrel burst and blow by. The static high pressure testing resulted in an average pressure of 310 psi with a standard deviation of 171 psi for EN063 PET. Potential failure modes were barrel burst and blow by. The static high pressure testing resulted in an average pressure of 305 psi with a standard deviation of 67 psi for HW CF746 PET. The failure mode was barrel burst.

Dynamic pressure testing was performed at 5 ml/s for 5 samples from each lot using saline. Dynamic pressure and capacitance testing were performed only for EN001 PET as the force to fail was the largest for that material of the three material types tested. In these tests, closed end 14' of syringes 10' was drilled out and a metal luer connection was connected. A flow restrictor valve was connected to the luer connection. The Instron was set at 5 ml/sec. The flow restrictor valve was adjusted to generate a pressure of 100 psi. The average dynamic friction force was 50 lbs or 18.7 psi at a syringe pressure of 100 psi.

In tensile strength testing, samples were first cut out using the tensile bar cutting die. Tests were then performed in accordance with the testing procedures set forth in ASTM D638. Samples were cut radially (5 samples of each lot) as well as axially (5 samples of each lot). FIG. 1E illustrates generally how axial and radial samples were cut from syringes 10. The results of several tensile strength studies are set forth in Table 2.

TABLE 2

|  | Maximum Stress (psi) | Stress @ Break (psi) | Stress @ Yield (psi) | Modulus (psi) | Strain @ Break | Strain @ Yield |
|---|---|---|---|---|---|---|
| 001 Axially | 16546 | 16216 | 10842 | 475964 | 52 | 3 |
| 001 Radially | 9146 | 5095 | 8914 | 344345 | 31 | 4 |
| 063 Axially | 13990 | 9632 | 11146 | 485791 | 39 | 3 |
| 063 Radially | 9214 | 1594 | 9196 | 353298 | 25 | 4 |
| HW Axially | 12024 | 7670 | 10409 | 527765 | 29 | 3 |
| HW Radially | 8440 | 4360 | 7642 | 527413 | 18 | 3 |

In several capacitance testing studies of the syringes of the present invention, a metal luer was installed in syringes 10' as described above, and syringes 10' were filled with water. A rubber O-ring plunger was inserted and the plunger was advanced until the front of the plunger was approximately 1 inch past drip flange 30. Syringe 10' was then mounted onto the Instron. The Instron was set to run at 2 in/min and to stop at a load of 540 lbs. A 3-way stopcock was installed on the end of the syringe, and a scale was placed under the syringe with a beaker to capture the fluid. A piece of connector tubing was attached to the metal luer fitting that was of sufficient length to reach into the beaker. Care was taken so that the tubing did not come in contact with the beaker. The Instron was then run. When the 540 lb limit was reached, the stopcock was turned slowly to dispense the fluid into the beaker. Subsequently, the stopcock was returned to the closed position to dispense the remaining fluid out of the line. The volume of fluid dispensed into the beaker was recorded. The results of several studies are set forth in Table 3.

TABLE 3

| Syringe # | Fluid Dispensed |
| --- | --- |
| 73 | 6.3 ml |
| 94 | 6.6 ml |
| 74 | 4.8 ml |
| 71 | 6.3 ml |

In general, neither the tested syringes or the method of manufacture was optimized in the above studies. The failure mode observed during the burst pressure tests, were almost all a result of splitting at the blow mold parting line. The blow mold parting line is the split between the mold halves. A non-optimized parting line can cause undue material stress and malformation, which may weaken this area. Optimizing the parting line (which was not done in the present studies) can, for example, be accomplished by ensuring a minimal mismatch and sharp clean edges on the parting line of the blow molding tool. The friction force and static pressure were found to be relatively consistent in the tested syringe with the highest level of consistency realized with the EN001 material. The data suggested that the blow-up ratio to tensile strength is a linear function, which correlates with published information on injection-stretch blow molding. These results reflect a 2 to 1 ratio on the axial dimension and a 1 to 1+ on radial dimensions. The EN001 material exhibited the highest increase. The friction force was found to consistent along the length of the barrel. Moreover, the barrel wall thickness was consistent, as interpolated from the friction data.

A "heat setting" process as known in the blow molding arts (effected, for example, via heating the blow mold cavities to elevated temperatures) may be desirable, for example, in the case that ethylene oxide (EtO) sterilization is to be used, as a result of the elevated temperatures used during EtO sterilization. The elevated temperatures of the EtO sterilization process may cause the suitable or acceptable dimension of the syringe barrel internal diameter to relax or change to an unacceptable dimension. The syringe plunger, which is sealingly and slidably positioned within the syringe barrel, exerts an outward force to ensure an adequate seal against the barrel wall to prevent leakage when pressurized during use. The heat setting process prevents the barrel wall from expanding or contracting and changing to an unacceptable dimension. It is not believed that a "heat setting" process will be required to control or improve the fluid capacitance of the syringe barrel. However, the results indicate that syringe fluid capacitance can also be improved with blow molding (for example, via heat setting), as compared to injection molding even with a relatively thin wall. The wall thickness of the syringes studied in the present invention was approximately 0.030 inches (versus, for example, approximately 0.79 for a typical injection molded syringe). The pressure capability of the syringe barrel can, for example, be improved by using a preform which exhibits a higher stretch ratio with the same wall thickness. The preform design can also be improved or optimized to, for example, take advantage of the PET "self leveling" material characteristics, which will improve dimensional consistency and increase overall material strength. In general, self leveling is the ability for the polymer to stretch, such that it pulls from a thicker cross section instead of a thinner cross section. If the cross section is properly sized to the total expansion, the final component will exhibit a consistent wall thickness.

FIGS. 2A through 2H illustrate another embodiment of a preform 210 and a blow molded, open-ended syringe 210'. As with preform 10, preform 210 is first molded using an injection molding process. The injection molded process facilitates the formation of areas in which dimensional tolerances are critical such as the injector attachment mechanism 220 on the rearward end of preform 210. In the embodiment of FIGS. 2A through 2H, injector attachment mechanism 220 includes a flange 222 that extends around the circumference of preform 210 and syringe 210'. In the illustrated embodiment, preform 210 and syringe 210' also include a drip flange 230. Syringe 210' can alternatively or additionally include other precision molded portions or sections. Once again, injector attachment or mounting flange 222 and drip flange 230 (and/or other precision molded portions) remain essentially unchanged from preform 210 to blow molded syringe 210'. A stretch rod 320 can be incorporated into the blowing mold process to induce biaxial orientation and to assist in, for example, ensuring that premolded features forward of the portion of preform 210 to be expanded such as illustrated in FIG. 2F and discussed further below are not harmed (for example, that the dimensions thereof are not substantially altered and required tolerances are maintained) during the blowing molding process. After the preform 210 is preheated as described above and placed into the blowing mold, two halves 305 of the blowing mold (see FIG. 2G) are closed. When properly clamped, stretch rod 320 is moved linearly to engage tip 330 into the internal aspect of syringe tip 214. Stretch rod 320 continues to move forward forcing syringe tip 214 into a protected mold area shaped in the form of syringe tip 214 and/or other forward precision molded component (see FIG. 2G). This area of the mold as well as the area encompassing mounting flange 222 and drip flange 230 can be maintained below molding temperature, so that the dimensions of the premolded syringe tip 214, the premolded mounting flange, and the premolded drip flange 230 are not affected/altered.

Similar to preform 10, preform 210 is placed within the mold, as illustrated in FIG. 2G, in which it undergoes stretch blow molding to result in syringe 210'. Preform 210 and syringe 210' included forward, open-ended syringe tip 214 including a syringe outlet 214a having an integrally or monolithically formed, precision molded connector such as a connector including a male luer taper and a luer threading 214b in the illustrated embodiment. Barrel 212' is connected to syringe tip 214 by a rounded (in cross section) transition region 216'. Mounting flange 222 and drip flange 230 cooperate with corresponding retaining flanges in the mold to retain the rearward end of preform 210 and syringe 210' throughout the stretch blow molding process.

As described above, during the stretch blow molding process, stretch rod 320 is extended forward, while compressed air is blown into the interior of preform 210 until preform 210 is expanded to fill the mold cavity, thereby manufacturing syringe 210' including barrel 212' in which the thermoplastic is biaxially oriented. In this embodiment, stretch rod 320 includes a forward section 330 dimensioned to enter and at least partially seal the rearward portion of syringe tip 214' (from fluid connection with the portion or preform 210 being expanded), thereby assisting in maintaining pressure within expanding barrel 212'. Stretch rod 320 also pushes against syringe tip 214' during the blow stretch molding process as described above to, for example, assist in achieving biaxial orientation. Moreover, stretch rod 320 at least partially prevents heated gas from entering syringe tip 214, (which is injection molded during fabrication of preform 210 to predefined acceptable tolerances), thereby assisting in maintaining syringe tip 214 essentially unaltered during the blow molding process.

FIG. 2H illustrates syringe 210' in operative connection with an injector including a controller and a motor in operative connection with the controller to control the powered motion of a drive member or piston 350 in operative connection with syringe plunger 250 which is slidably positioned within syringe barrel 212'. As described above, injectors suitable for use with various syringes of the present invention are disclosed, for example, in U.S. Pat. No. 5,383,858 and U.S. Pat. No. 6,652,489.

FIG. 2H also illustrates that the wall of syringe 210' can include a first layer 212a' of a first polymeric material and at least a second layer 212b' of a second polymeric material, different from the first polymeric material. At least one of the first polymeric materials can, for example, include polyethyleneterephthalate, cyclic olefin polymer, polypropylene, polystyrene, polyvinylidene chloride, polyethylene naphthalate and/or nylon. The second polymeric material can, for example, be nylon, ethylene vinyl alcohol copolymer (EVOH), polycarbonate or other suitable polymers as known in the art. EVOH, for example, provides good barrier properties and may be used in connection, for example, with prefillable syringes. The first and/or the second polymeric material can, for example, include a single polymer or blends of two or more polymers. The polymeric materials of the first layer and the second layer can, for example, differ in one or more respects such as composition, molecular weight, crystallinity, barrier properties etc. As known in the blow molding arts, an adhesive or tie layer 212c' can be used between polymeric layers to strengthen the bond between such layers. Suitable adhesives or tie layers include those known in the art that are useful in adhering layers of dissimilar polymeric materials and in achieving an improved interlayer bond strength. An example of a suitable adhesive or tie layer material is ADMER® (a modified polyolefin with functional groups available from Mitsui Chemicals America, Inc. of Rye Brook, N.Y.) that is suitable to bond to a variety of polymers including, for example, polyolefins, ionomers, polyamides, ethylene vinyl alcohol (EVOH), PET, polycarbonates, and polystyrenes.

In general, the process described above in connection with the syringe of FIGS. 2A through 2H can be used to create any hollow device or apparatus that is open at both ends via a blow stretch molding process. The process is thus well suited for fabricating many fluid flow path elements used, for example, in the medical arts. As used herein, the term "flow path element" refers generally to any device or element through which a fluid (for example, a liquid and/or gas) flows (for example, in a medical systems). Such flow path elements are open at each end and at least one end thereof, and often each ends thereof, includes an attachment mechanism and/or or other portion or section molded to certain predefined acceptable tolerances to, for example, enabling attachment of the flow path element to other devices and/or flow path elements. As known in the art, connector or attachment mechanisms can take a wide variety of forms (for example, threaded attachments, snap attachments, friction attachments, Luer attachments, plug fits etc.). As also known in the art, it is desirable to mold such connector or attachment mechanism or mechanisms within specific tolerances to, for example, ensure a non-leaking, high-pressure seal. As described above, the blow stretch molding processes and systems of the present invention are well suited to expand the intermediate portion or section of the device or flow path element while the dimensions and other properties of the precision molded portions on one or both ends of the device are essentially unaltered. In that regard, the blow stretch molding methods and systems of the present invention are suited to maintain common production tolerances (both fine and commercial standards) for a wide variety of polymeric materials as described, for example, in Whitmore, E. M., editor, Standards & Practices of Plastics Molders—Guidelines for Molders and Their Customers, Molders Division, Sponsored by the Society of the Plastics Industry, Inc. (1993). The blow stretch molding methods and systems of the present invention are, for example, suitable to maintain tolerances of end attachments or other molded features to plus or minus 0.05, 0.02, 0.01, 0.005 and even 0.002 for a variety of polymeric materials.

FIGS. 2I and 2J illustrate examples of fully formed flow path elements and devices that can be fabricated using the blow stretch molding methods of the present invention. FIG. 2I illustrates a flow path element 360 (for example, a drip chamber) having an inlet 362 and an outlet 364. Each of inlet 362 and outlet 364 are injection molded to incorporated precision molded connection or attachment mechanisms before the blow stretch molding process. In that regard, inlet 362 includes a threaded connection in the vicinity thereof, and outlet 364 includes a male Luer connection in the vicinity thereof. The dimensions/tolerances of the precision molded connection mechanisms (and/or other precision molded components) are essentially unaltered during the expansion of intermediate (hollow) section 366 during the blow stretch molding process.

FIG. 2I illustrates an embodiment of a low-pressure, manually operated syringe 370 formed by a blow stretch molding process of the present invention. Syringe 370 includes a rearward or proximal opening 372 and a forward or distal outlet 374 in the form of a male Luer fitting. A manually operated plunger extension 380 connects to syringe plunger 382 slidable positioned within syringe barrel 376 through rearward opening 372. Syringe 370 further include finger grips 378. The dimensions/tolerances of the Luer connector finger grips 378 are essentially unaltered during the expansion of syringe 376 during the blow stretch molding process.

FIGS. 3A and 3B illustrate another embodiment of a syringe 410' of the present invention which is blow molded from a preform (not shown). In this embodiment, syringe 410'. includes a rear mounting flange 422 and a forward syringe tip 414 that remain essentially unchanged during the blow molding process. As described above, barrel 412' and transition region 416' are expanded to fill the mold cavity during the blow molding process.

In this embodiment, syringe tip 414 includes an integrally molded syringe tip closure 418 that is molded integrally with syringe tip 414 during the injection molding of the preform. Syringe tip closure 418 can, for example, be connected to syringe outlet 414a via an area of reduced wall thickness 419 so that syringe tip closure 418 can be readily broken off to open syringe outlet 414a. Syringe tip closure 418 can, for example, assist in maintaining sterility in the case of a prefilled syringe. The integrally molded syringe tip closures of the present invention can also be provided on syringes that are not blow molded (for example, injection molded syringes).

FIGS. 4A and 4B illustrate another embodiment of a syringe 510' of the present invention blow molded from a preform (not shown). In this embodiment, syringe 510' includes a rear mounting flange 522 and a forward syringe tip 514 that remain essentially unchanged during the blow molding process. As described above, barrel 512' and transition region 516' are expanded to fill the mold cavity during the blow molding process. In the embodiment of FIGS. 4A through 4B, compressed air can, for example, be blown into the preform through syringe tip 514a to create the rearward, integral or monolithic closure/plunger cover 540 in a blow molding process. Extrusion blow molding can, for example, be used in this embodiment.

With reference to FIG. 4B, in several embodiments, closure 540 is removable at edges 542 thereof (for example, via areas of reduced wall thickness, channels, notches etc.) from the connection with the remainder of syringe 512'. As described above, the removable closure can, for example, form a plunger section upon removal from connection with the remainder of syringe 512'. Plunger or plunger cover 540 forms a substantially sealing engagement with the inner wall of syringe 512' when slid through the barrel thereof. In the illustrated embodiment, plunger 540 includes a flange 544 attached at a rearward portion of flange 544 to body or central portion 548 of the plunger 540. Flange 544 extends forward and radially outward to form a circumferential channel 546 between flange 544 and body 548 of plunger 540. During use of syringe 512', fluid within syringe 512' enters annular channel 546. Forward motion of plunger 540 to pressurize and inject fluid contained within syringe 512 results in pressurization of the fluid within annular channel 546. The hydraulic force of the fluid within annular channel 546 forces flange 544 away from body portion 548 and against an inner wall of syringe 512'. As plunger 540 is moved forward, flange 544 is forced against the inner wall of syringe 512' and prevents any fluid from passing rearward between flange 544 and the inner wall of syringe 512'. The operation of plungers including such a "wiper seal" is discussed, for example, in U.S. Pat. No. 6,224,577.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

What is claimed is:

1. A syringe for use in a pressurized injection of a fluid, the syringe comprising:
    a blow-molded syringe barrel formed of a polymeric material, the syringe barrel having a consistent wall thickness and capable of withstanding pressures of at least 1200 psi and formed by a blow-molding process; and
    an injection molded attachment mechanism integral with the syringe barrel and located at a proximal end of the syringe barrel,
    wherein the syringe barrel comprises a biaxial stretch sidewall as a result of the blow-molding process while the attachment mechanism remains essentially unchanged as a result of the blow-molding process.

2. The syringe of claim 1, wherein the biaxial stretch sidewall of the syringe barrel comprises an inner diameter that does not vary by greater than 0.01 inches.

3. The syringe of claim 1, wherein the biaxial stretch sidewall of the syringe barrel comprises an inner diameter that does not vary by greater than 0.007 inches.

4. The syringe of claim 1, wherein the biaxial stretch sidewall of the syringe barrel comprises an inner diameter that does not vary by greater than 0.004 inches.

5. The syringe of claim 1, wherein the polymeric material is selected from the group consisting of polyethyleneterephthalate, cyclic olefin polymer, polypropylene, polystyrene, polyvinylidene chloride, polyethylene naphthalate, nylon, and combinations thereof.

6. The syringe of claim 1, wherein the syringe barrel comprises a first layer of a first polymeric material and at least a second layer of a second polymeric material, different from the first polymeric material.

7. The syringe of claim 1, wherein the syringe barrel has a consistent wall thickness of less than 0.05 inches.

8. The syringe of claim 1, wherein the syringe barrel has a consistent wall thickness of less than 0.07 inches.

9. A syringe comprising:
    a blow-molded syringe barrel formed of a polymeric material;
    an outlet section integrally formed with the syringe barrel at a distal end of the syringe barrel;
    an injection molded attachment mechanism integrally formed at a proximal end of the syringe barrel; and
    a removable closure integrally molded with the outlet section at a distal end of the outlet section during an injection molding process,
    wherein the syringe barrel comprises a biaxial stretch sidewall as a result of the blow-molding process while the attachment mechanism remains essentially unchanged as a result of the blow-molding process.

10. The syringe of claim 9, wherein the removable closure is removably connected to the outlet section via a wall section of reduced thickness.

11. A syringe comprising:
    a blow-molded syringe barrel formed of a polymeric material;
    an outlet section integrally formed on a distal end of the syringe barrel;
    an injection molded attachment mechanism integrally formed with a proximal end of the syringe barrel; and
    a removable closure integral with the proximal end of the syringe barrel and formed during the blow-molding process,
    wherein the syringe barrel comprises a biaxial stretch sidewall as a result of the blow-molding process while the attachment mechanism remains essentially unchanged as a result of the blow-molding process.

12. The syringe of claim 11, wherein the removable closure comprises a sealing member that forms a seal with an inner wall of the syringe barrel.

13. The syringe of claim 11, wherein the removable closure comprises a flange that forms a wiper seal with an inner wall of the syringe barrel.

14. A syringe comprising:
    a blow-molded syringe barrel formed of a polymeric material and comprising a side wall having a first layer of a first polymeric material extending radially inward from a second layer of a second polymeric material, wherein the first layer has a greater lubricity than the second layer and wherein at least one of the first layer or the second layer is capable of withstanding pressures of at least 1200 psi; and
    an injection molded attachment mechanism integrally formed with a proximal end of the syringe barrel,
    wherein the side wall of the syringe barrel comprises a biaxial stretch orientation as a result of the blow-molding process while the attachment mechanism remains essentially unchanged as a result of the blow-molding process.

15. The syringe of claim 6, wherein the first polymeric material and the second polymeric material are independently selected from the group consisting of polyethyleneterephthalate, cyclic olefin polymer, polypropylene, polystyrene, polyvinylidene chloride, polyethylene naphthalate, nylon, and combinations thereof.

16. The syringe of claim 14, wherein the first polymeric material is selected from the group consisting of polyethyleneterephthalate, cyclic olefin polymer, polypropylene, polystyrene, polyvinylidene chloride, polyethylene naphthalate, and nylon.

17. The syringe of claim 14, wherein the second layer has better barrier properties than the first layer.

18. The syringe of claim 14, further comprising a tie layer between the first layer and the second layer.

19. The syringe of claim 14, wherein the second polymeric material is selected from the group consisting of nylon, ethylene vinyl alcohol copolymer (EVOH), and polycarbonate.

20. The syringe of claim 14, wherein at least one of the first layer or the second layer has a thickness of less than 0.07 inches.

* * * * *

UNITED STATES PATENT AND TRADEMARK OFFICE
CERTIFICATE OF CORRECTION

PATENT NO.        : 8,939,940 B2                                   Page 1 of 1
APPLICATION NO.   : 12/794990
DATED             : January 27, 2015
INVENTOR(S)       : Haury et al.

It is certified that error appears in the above-identified patent and that said Letters Patent is hereby corrected as shown below:

IN THE SPECIFICATION:

In Column 10, Line 29, delete "syringes 10." and insert -- syringes 10'. --, therefor.

Signed and Sealed this
Sixteenth Day of June, 2015

Michelle K. Lee
*Director of the United States Patent and Trademark Office*